(12) United States Patent
Loeb

(10) Patent No.: US 6,887,667 B2
(45) Date of Patent: May 3, 2005

(54) METHOD AND APPARATUS TO IDENTIFY SMALL VARIATIONS OF BIOMOLECULES

(75) Inventor: Gerald E. Loeb, South Pasadena, CA (US)

(73) Assignee: Alfred E. Mann Institute for Biomedical Engineering at the University of Southern California, Los Angeles, CA (US)

(*) Notice: Subject to any disclaimer, the term of this patent is extended or adjusted under 35 U.S.C. 154(b) by 155 days.

(21) Appl. No.: 10/025,095

(22) Filed: Dec. 18, 2001

(65) Prior Publication Data

US 2002/0119481 A1 Aug. 29, 2002

Related U.S. Application Data

(60) Provisional application No. 60/258,893, filed on Dec. 28, 2000.

(51) Int. Cl.⁷ .................. C12Q 1/68; C12P 19/34; C07H 21/00
(52) U.S. Cl. ............ 435/6; 435/7.1; 435/91.1; 435/91.2; 536/22.1; 536/23.1; 536/24.3; 536/24.33
(58) Field of Search .................. 435/6, 7.1, 91.1, 435/91.2; 536/221, 23.1, 24.3–24.33

(56) References Cited

U.S. PATENT DOCUMENTS

| | | |
|---|---|---|
| 4,591,550 A | 5/1986 | Hafeman et al. |
| 5,500,188 A | 3/1996 | Hafeman et al. |
| 5,643,721 A | 7/1997 | Spring et al. |
| 5,645,709 A | 7/1997 | Birch et al. |
| 5,653,939 A | 8/1997 | Hollis et al. |
| 5,683,569 A | 11/1997 | Chung et al. |
| 5,685,969 A | 11/1997 | Hoenig et al. |
| 5,719,033 A | 2/1998 | Ackley et al. |
| 5,753,518 A | 5/1998 | Karlsson |
| 5,858,799 A | 1/1999 | Yee et al. |
| 5,891,630 A | 4/1999 | Eggers et al. |
| 5,906,921 A | 5/1999 | Ikeda et al. |
| 5,942,388 A | 8/1999 | Willner et al. |
| 5,951,846 A | 9/1999 | Lewis et al. |
| 5,965,410 A | * 10/1999 | Chow et al. ............... 435/91.2 |
| 5,981,203 A | 11/1999 | Meyerhoff et al. |
| 6,093,308 A | 7/2000 | Lewis et al. |
| 6,218,121 B1 | 4/2001 | Simpson et al. |

OTHER PUBLICATIONS

International Search Report dated Jul. 2, 2002 from the corresponding PCT International Application PCT/US01/49778.

* cited by examiner

*Primary Examiner*—Jezia Riley
(74) *Attorney, Agent, or Firm*—McDermott Will & Emery LLP (57) ABSTRACT

Many diseases are related to variations in the genetically specified structure of proteins synthesized by cells. Genetic engineering is now able to identify the structural variations and to introduce new genes to synthesize more healthful proteins, but it is difficult actually to identify the specific protein or chemical variants in bodily fluids and extracts of tissues in order to diagnose diseases and to assess the effects of treatment. This invention provides apparatuses and methods which allow a user to finely discriminate between small variations in the structure, function and levels of specific biochemicals even when admixed with other biochemicals.

13 Claims, 3 Drawing Sheets

METHOD AND APPARATUS TO IDENTIFY SMALL VARIATIONS OF BIOMOLECULES

RELATED APPLICATIONS

This application claims priority of U.S. provisional application Ser. No. 60/258,893, filed Dec. 28, 2000, which is incorporated by reference into this application.

BACKGROUND OF THE INVENTION

This invention relates to a method and device for identifying biomolecular variants. In particular, the invention is concerned with a method for detecting the presence and quantities of biomolecular variants admixed in a sample. Detection of biomolecular variants is accomplished indirectly by assaying the activity of the variants in a sample via reaction product production and/or binding or reaction kinetics with a reactant.

Many diseases are related to variations in the genetically specified sequences of biomolecules. For example, point mutations in a gene can result in the production of a protein variant having an altered structure, and consequently altered activity. This change in protein structure, relative to the native protein molecule, may alter the protein's function as an enzyme, transmitter or antigen, for example, in a manner that directly causes disease. In other cases, the presence of a particular protein variant is a predisposing risk factor or genetic marker for disease. Further, a patient's health or disease is related to the amounts of biomolecules rather than the precise mutation or presence or absence of a biomolecular variant due to gene expression. Thus, it is desirable to have an assay to detect biomolecular variants to diagnose and treat various disease states.

Current molecular biological techniques enable the identification and quantification of biomolecular variants once isolated (for example, by sequencing genes encoding or the amino acids comprising a protein). However, isolating biomolecular variants biomolecules is often difficult. First, biomolecules and their variants are admixed with many different biomolecule populations in body fluids and tissue extracts. Second, the physical properties by which biomolecules are currently isolated (molecular weight, size and charge) are often unchanged or only subtly changed in the mutant variants.

One common laboratory strategy for separating and identifying individual biomolecules from mixtures of large numbers of different biomolecules is to utilize subtle differences in the physical chemistry of those biomolecules to separate them spatially on a surface. For example, chromatographic techniques are used to separate biomolecules based on their molecular weight and diffusibility. This technique can be combined with an orthogonal gradient based on the tendency of the biomolecules to migrate under the influence of an electrical field at a rate proportional to their intrinsic charge. Once separated spatially, localized concentrations of specific biomolecules can be identified, for example by staining them non-specifically for the presence of proteins or nucleic acids or specifically using antibody reactions. However, mutant variants of biomolecules often do not differ sufficiently from native variants in molecular weight, diffusibility or intrinsic charge to be physically separable and identified with these methods.

Currently, the most selective detection methodologies used to detect the presence and quantity of biomolecular variants involve molecule specific binding, between enzymes and substrates or between antigens and antibodies, for example. However, even these molecule-specific reactions often cannot distinguish between small biomolecular variations, such as those caused by point genetic mutations. Thus, assay methods which allow biomolecular variants to be distinguished for identification and quantification are desired.

Mutant variants are more likely to be distinguishable from native variants by their function than their physical chemistry. Biomolecular function is proportionate to a molecule's reaction kinetics with other biochemicals, such as metabolic substrates, degradative enzymes and antibodies. Indeed, these altered reaction kinetics are often related to the pathophysiology of the diseases with which biomolecular variants are associated.

Biomolecular variants can be detected and quantified once spacially or functionally isolated. Sensor arrays for electrochemically detecting the presence and/or reaction kinetics of analytes and biomolecules in solution are described, for example, in U.S. Pat. Nos. 5,891,630, 5,942,388 and 5,951,846, 5,981,203, 5,942,388, 5,906,921, 5,858,799, 5,719,033, 5,753,518, 5,643,721, 5,645,709, 5,653,939, 5,683,569, which are incorporated herein by reference and such technologies may be useful in the present invention. Optically scanned arrays for detecting the binding of biomolecules are also well-known, for example, so-called DNA or microarray chips. However, there appears no method that systematically alters the reaction kinetics between two biomolecular variants so as to detect the presence or quantify variants of interest. Thus, it is desirable to utilize a method and device to create conditions by which biomolecular variants can be distinguished and quantified to create a rich set of data from which it is possible to distinguish the presence of one or more variants and to quantify the absolute and relative concentrations or amounts of such variants in a sample.

SUMMARY OF THE INVENTION

This invention provides a method and device for identifying and quantifying biomolecular variants having similar physical properties in a sample containing an unknown admixture of such variants. The method includes multiple sites for the measurement of the amount or rate of binding or reaction between the sample and a reactant, in which each site lies in a different position along a gradient of imposed conditions that affect the rate of binding or reaction. This method is advantageous over other methods in that biomolecules having single nucleic acid or amino acid sequence differences can be differentiated and quantified as a result of molecular differences enhanced by the imposed gradients on variant binding to or reactions with a reactant.

More specifically, the methods for the identification and quantification of admixtures of two or more biomolecular variants involve: a) applying of at least one condition gradient upon a detection array, wherein the gradient conditions affect the (rate of binding or reaction) between the biomolecular variants and a reactant; b) measuring of the (time-varying amount or rate of binding or reaction) between each biomolecular variant and the reactant at discrete locations of a gradient axis; c) analyzing measurements of the (time-varying amount or rate of binding or reaction) from the discrete locations along a gradient axis mathematically to determine the relative or absolute quantities of each variant present in the mixture. The gradient conditions which may be selected include pH gradients, light gradients and or temperature gradients.

This method also employs a device for carrying out the methodology above. The device may include elements which create gradient conditions to further differentiate the reaction kinetics of the biomolecules being assayed. Specifically, the device may include elements which alter biomolecular function by altering inherent charge of the variants being assayed, for example by generating a pH gradient along a sample array. Alternatively or in addition, the biomolecular function may be systematically altered by creating a gradient of temperature or absorbed light (ex. bombardment the reacting chemicals with photons at a range of wavelengths), either of which changes the energy of the reacting biomolecules. All of these techniques are capable of changing the stereochemical conformation of biomolecules, which, in turn, change the kinetics of the binding or reaction being assayed.

The device may employ an array of electrochemical and/or photochemical detectors to quantify reaction kinetics of binding or reaction being assayed.

Further, digital data processing techniques, including learning or adaptive algorithms; may be used to identify and distinguish variants in solution according to the signals produced by an array or arrays of detectors.

The foregoing and other objects, features, and advantages of the present invention will be apparent from the following detailed description of the preferred embodiments which makes reference to several drawing figures.

DETAILED DESCRIPTION OF THE PREFERRED EMBODIMENTS

In the following description of the preferred embodiments reference is made to the accompanying drawings which form the part thereof, and in which are shown by way of illustration of specific embodiments in which the invention can be practiced. It is to be understood that other embodiments can be utilized and structural and functional changes can be made without departing from the scope of the present invention.

The present invention is designed for the high resolution detection and quantification of a population of biomolecular variants having small differences in their composition. The differences may be as small as a single point mutation, leading to a single amino acid difference between protein variants, for example. This methodology provides for the separation and detection of biomolecular variants with a resolution that has not been possible by prior or conventional methods, short of sequencing at the DNA or amino acid level.

Samples to be assayed include biological samples containing biomolecules obtained from patient tissue or fluid specimens. Further, samples may include specimens from which biomolecules have been separated or isolated using standard laboratory technology (such as cellular fractionation; gel or ion chromatography, or electrophoresis). Biomolecules which may be detected using the methods and device of this invention, include, but are not limited to native or mutant DNA, RNA, proteins and prions.

Method of Variant Detection

Figure 1:
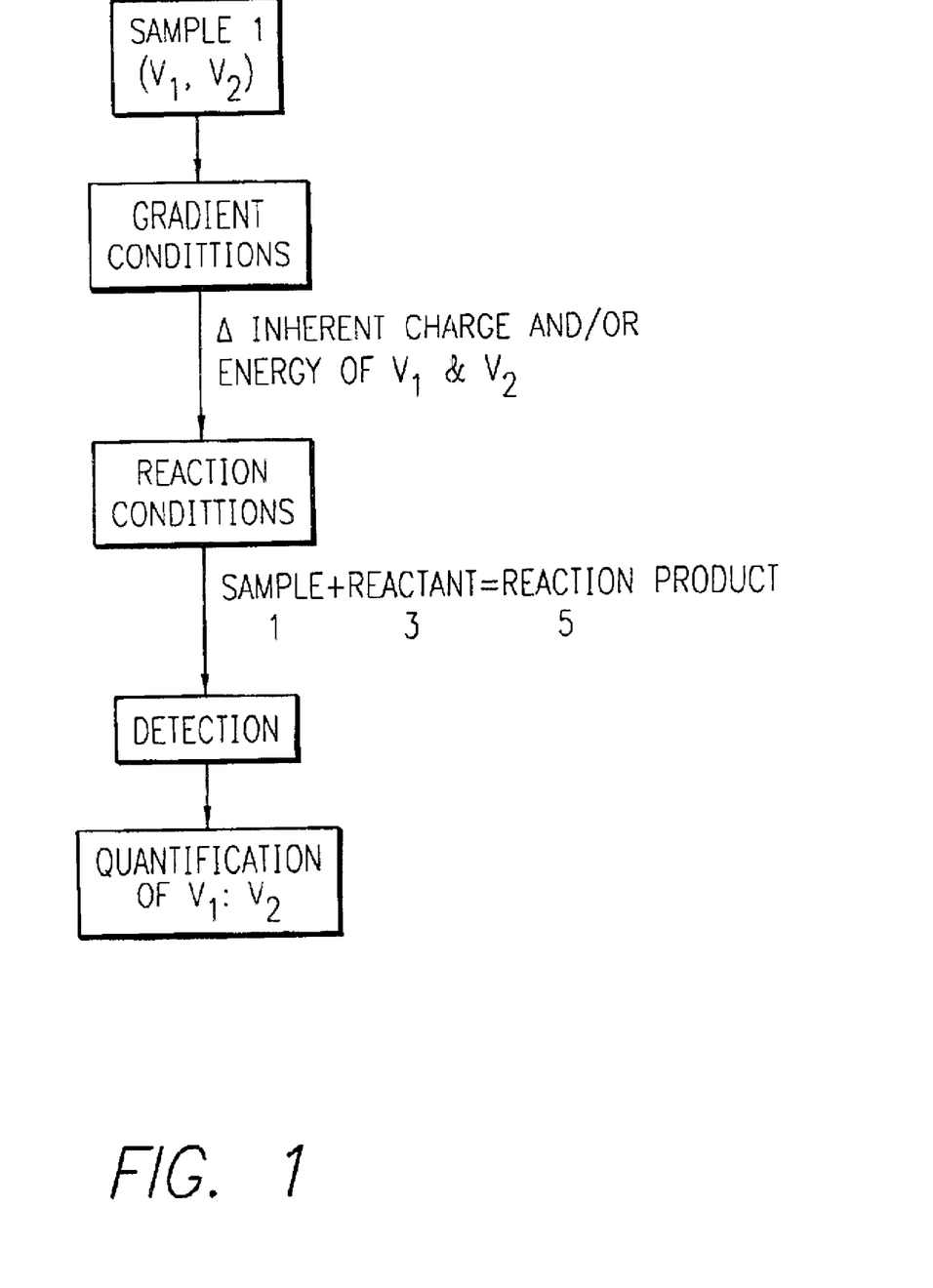
FIG. 1 is a flow chart depicting the general methodology of the invention.

The methods of this invention are directed to the indirect detection and quantification of at least two different biomolecular variants (V1, V2, etc.) and operate by assaying the activity of the variants with a known reactant. Further, the method advantageously maximizes the differential activity of the variants by utilizing at least one gradient condition to improve the resolution of the assay. The general approach of the method is illustrated in FIG. 1.

First, the method involves exposing the sample to at least one gradient condition that affects the rate or amount of binding or reaction between the biomolecular variants and a reactant along a gradient axis. Where more than one gradient condition is used it is preferable that the gradient axes lie at angles to one another, and are preferably perpendicular to one another, to further maximize differentiation of the variants being detected.

Gradient conditions which may be used in the method include those which alter 1) the inherent charge and/or 2) the inherent energy of the variants being assayed such as pH gradients, light gradients and or temperature gradients.

One example of a method which may be used to alter the inherent charge of the variants in the sample is the generation of a pH gradient. The kinetics of binding between biomolecules in an aqueous solution is usually governed by electrostatic van der Waals forces between oppositely charged regions of those molecules that tend to align with each other to effect the chemical binding between the molecules. Small changes in the ambient concentration of hydronium and hydroxyl ions by changing the pH of the solution tends to cause relatively large changes in the kinetics of binding because of small conformational changes in and/or neutralization or enhancement of surface charges on one or both of the biomolecules. A pH gradient may be generated such that opposing regions of a sample are provided with positive and negative energy inputs, as detailed below, such that areas of higher pH and areas of lower pH are created on a substrate.

A second example of a method which may be used to alter the inherent energy of the variants in the sample is creation of a gradient of absorbed light. Many biomolecules tend to absorb photons of a particular wavelength or can be made to selectively absorb such photons by attachment of dye molecules. When photons are absorbed, the energy added to the molecule may induce conformational or charge distribution changes that affect the kinetics of its binding to another molecule. The gradient of absorbed light could be in terms of a gradient of wavelengths of light such as can be produced by a prism or other diffractive separation applied to a broadband source of light, or a tunable source of monochromatic light such as a nitrogen laser or laser diode. The gradient of absorbed light absorption could be in terms of a gradient of photon flux such as can be produced by an obliquely illuminating beam or an interposed filter with a gradient of optical density.

A third example of a method which may be used to alter the rate or amount of binding or reaction is creation of a gradient of temperature along a surface. This may be accomplished most simply by heating the substrate on which the reactions occur from one edge, such that areas of higher temperature and areas of lower temperature are created.

Second, the method involves measuring of the (time-varying amount or rate of binding or reaction) between each biomolecular variant and a reactant at discrete locations of a gradient axis. For example, a sample containing variants (V1, V2, etc.) may be contacted with a reactant biochemical that specifically interacts with the variants to be assayed.

The reactant is preferably selected such that the reactant specifically interacts with all variants of the population to be assayed, and interacts to a minimal degree with other biomolecules which may be present in the sample. The reactants preferably have an affinity of at least two times greater for the variant population to be detected than for other biomolecules present in the sample, and more preferably an affinity of at least ten times greater for the variant population to be detected than for other biomolecules present in the sample. Such reactants may include but are not limited to, antibodies or proteins which interact specifically with protein variants, binding domain proteins which interact specifically nucleic acid variants, and complimentary nucleic acids which interact specifically hybridize with nucleic acid variants.

Further, the reactant is preferably selected such that when the sample is exposed to the reactant, the reaction between the sample variants and the reactant generates a reaction product that can be measured. The reaction product may be a binding pair of a variant and a reactant or may be a third molecule which results from the interaction of the variant with the reactant. One example of a reaction product that can be measured electrically is hydrogen peroxide, which is produced by the reaction between glucose and glucose oxidase and which can be detected by the current produced by its electrochemical reduction at the surface of a positively polarized platinum electrode. One example of a binding reaction that can be measured photonically is the binding of oxygen to hemoglobin, which changes the absorption of visible light by the hemoglobin. Another example of a reaction product that can be measured photonically is NADH, the end product of many metabolic reactions, which absorbs light at 340 nm wavelength and fluoresces at 460 nm.

Next, the reaction product (or rate of binding or reaction) can be detected and quantified. This measurement is a direct function of the reaction kinetics of each variant with the selected reactant, and an indicator of the quantity of the variant present in the sample. The reaction products can be measured by electrochemical or photochemical methods, for example.

The electrochemical detection methods may involve the measurement of electrical signals, including but not limited to, oxygen or hydrogen absorption, redox potentials, cyclic voltammetry currents. These electrical signals are preferably detected and recorded from an electrode located in proximity to the reaction products.

The photochemical detection methods can measure changes in the absorption or fluorescent emission of light. Measurements can be imaged and analyzed quantitatively according to the luminance and/or colors of the reaction products. For example, photochemical detection methods may involve chemically coupling a reactant or reaction product to a dye molecule, illuminating the reaction product with the appropriate wavelength(s) and intensity of light, recording a digital video image of the reaction product and tracking changes over time in the pixels that correspond to regions of interest in the video image. Methods for imaging, recording and spatially analyzing the time-varying fluorescence of calcium sensitive dyes are used routinely to track the activity of the living nervous system, for example.

Finally, the method involves analyzing measurements of the (time-varying amount or rate of binding or reaction) from the discrete locations along a gradient axis mathematically to determine the relative or absolute quantities of each variant present in the mixture.

Devices for Variant Detection

A device is preferably designed to maximize gradient conditions for the differentiation of variants, detection of reaction products, and quantification of the variants within a sample. Examples of devices which may be useful in this invention are the detection arrays 7 illustrated in FIGS. 2 & 3.

Figure 2:
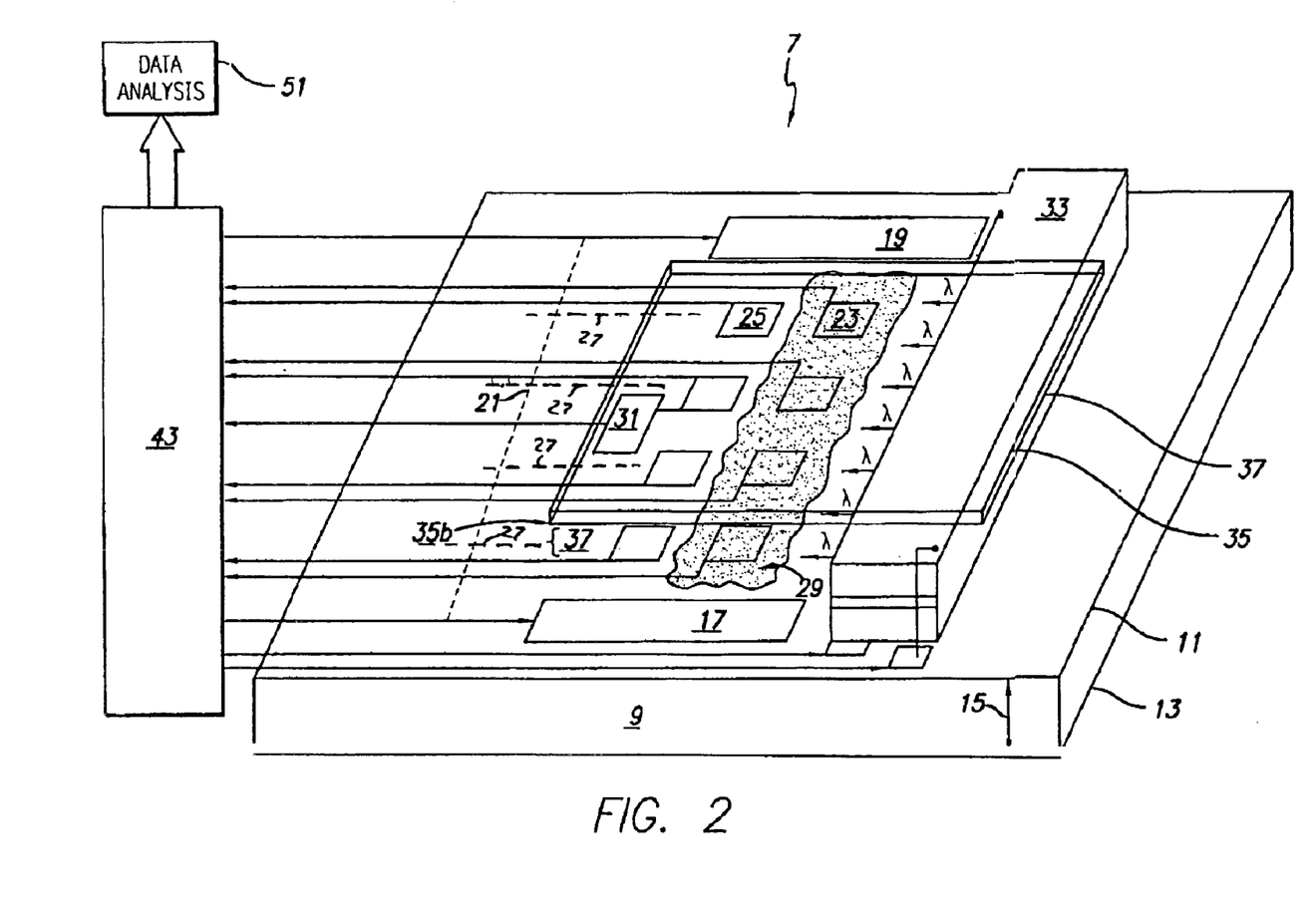
FIG. 2 is a perspective view of one embodiment of the device useful in practicing the invention.
Figure 3:
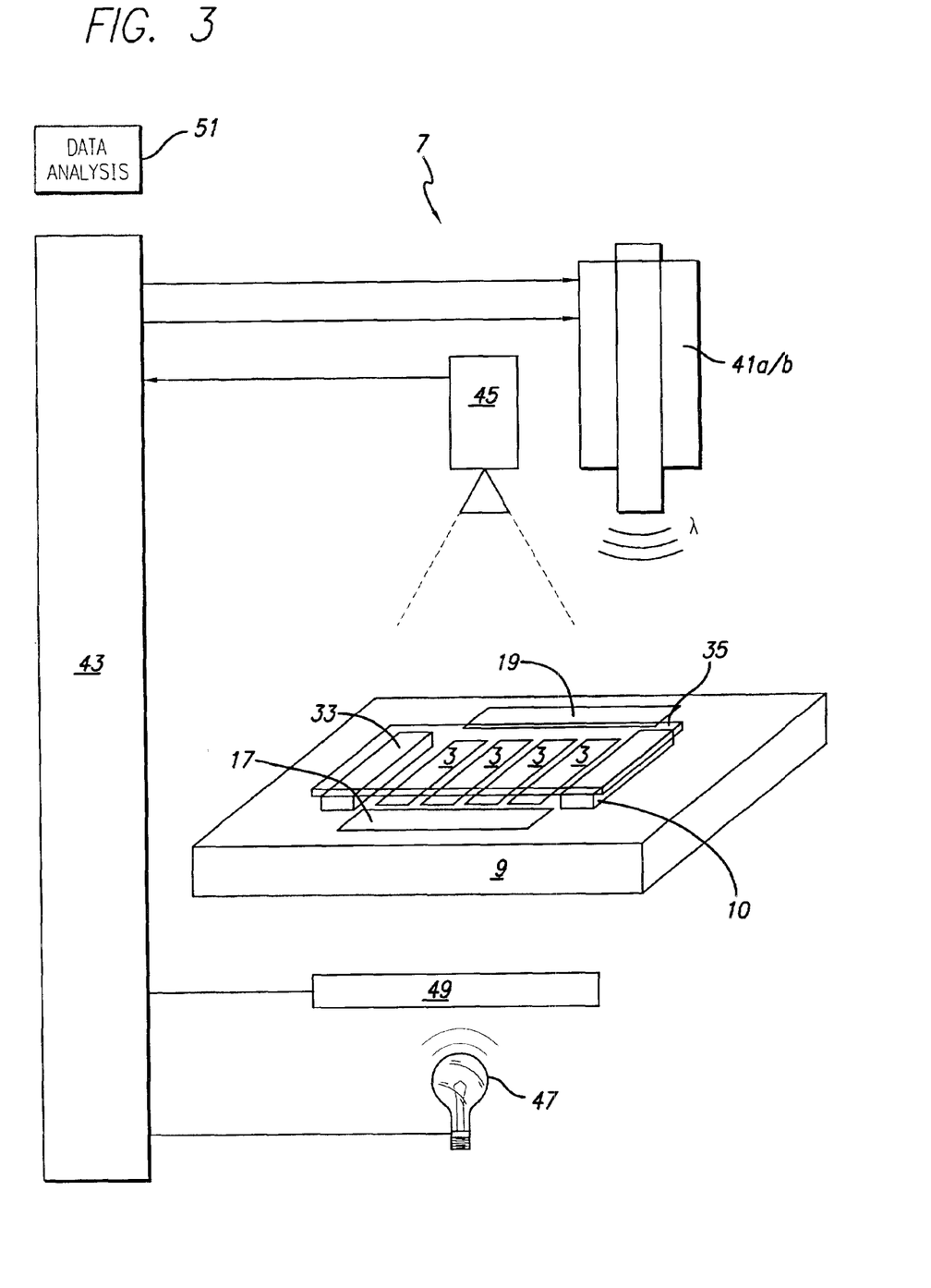
FIG. 3 is a perspective view of an alternate embodiment of the device useful in practicing the invention.

The methods described are preferably performed on the upper surface area of the substrate 11, however, the device and methods could be modified such that the method occurs within a reaction chamber 37 created within the substrate thickness 15 or on the lower surface area 13 of the substrate 9.

The substrate 9 materials which are useful for the detection array 7 are preferably selected for properties of optical transparency, chemical inertness, electrical resistivity, mechanical smoothness and/or adhesion of the reactant and include, but are not limited to silicon, alumina, glass or quartz.

Electrochemical Detection

In one embodiment of the invention, reaction product detection is accomplished by electrochemical means (FIG. 2). In this embodiment, a plurality of electrodes are disposed on the substrate upper surface area 11 for the creation of gradient conditions, as well as detection of reaction products. Such electrodes can be produced directly on the substrate 9 or produced and attached to the substrate 9, for example, by microelectronic photolithography. The electrode materials which are useful in the detection array 7 are preferably selected to act both as a stable source of electrolytic currents, and as a detector of various electrochemical reactions. One example of such a material is platinum.

The electrodes are preferably configured on the substrate 9 so as to maximize gradient conditions for the differentiation of variants and detect reaction products or reaction kinetics.

In this embodiment, the gradient conditions may be created by at least one pair of gradient electrodes 17/19 spaced a distance apart on a gradient axis 21 along the substrate upper surface area 11. The pair of gradient electrodes 17/19 are operated as electrolytic cathode and anode, respectively, by applying a direct electrical current between them. This induces a chemical reaction at cathode electrode that produces hydrogen gas from water, leaving behind an increased concentration of hydroxyl ions that creates an alkaline pH. The converse chemical reaction at anode produces oxygen gas from water, leaving behind an increased concentration of hydronium ions that creates an acidic pH. Due to diffusion forces, a pH gradient is created along the gradient axis 21, such that the areas of the gradient axis 21 closest to the gradient electrodes 17/19 experience the greatest change in pH. The steepness of the pH gradient may be altered by adjusting the nature and quantity of buffering agents in the sample and the magnitude of the electrolytic current applied between gradient electrodes 17/19.

In this embodiment, the detection of reaction products or reaction kinetics is accomplished by at least two pair of detection electrodes 23/25 spaced a distance apart on reaction axes 27 along the substrate upper surface area 11. The detection electrodes 23/25 are preferably spaced such that the reaction axes 27 lie perpendicular to the gradient axes 21.

As shown in this embodiment, detection electrodes 23/25 are arranged in parallel rows. The first detection electrode 23 is preferably covered with a reaction matrix 29 which contains at least one reactant. The reaction matrix 29 may be selected to the reactant from diffusing away from the surfaces of electrodes, and may be comprised of a reactant embedded in a hydropolymer, sol-gel glass or other matrix that is permeable to the variant sample and preferably to the reaction products to be detected by detection electrodes. The reaction matrix 29 may be formed in a continuous body which covers all detection electrodes or may be formed in discontinuous regions located in proximity to individual detection electrodes.

The second detection electrode 25 is preferably directly exposed to the sample and resulting reaction products. Finally, a reference electrode 31 is preferably placed in proximity to the detection electrodes 23/25, so as to provide a known reference potential for potentiostatic measurements performed with respect to various detection electrodes 23/25.

Still referring to FIG. 2, preferably a support 33 is placed on the substrate upper surface area 11 so as to suspend a sample distributor 35 at a plane above the substrate upper surface area 11 and preferably, substantially parallel to the substrate upper surface area. The support 33 may be integrally formed with the substrate 9 or may be formed separately and attached to the substrate upper surface area 11. Further, the sample distributor 35 may be a glass coverslip, for example, that in part forms a reaction chamber 37, and acts to create a thin layer of the sample by capillary action and surface tension.

This arrangement is such that a reaction chamber 37 is created between the substrate 9 and sample distributor lower surface area 35b, such that when the sample is applied to one side of the reaction chamber 37, it will move according to capillary action so as to fill completely reaction chamber 37. This configuration assists the sample in contacting with all detection electrodes 23/25 and improves the linearity and predictability of gradient conditions along rows of detection electrodes 23/25 described above. The sample distributor 35 preferably does not extend over the gradient electrodes 17/19, thereby permitting electrolysis byproducts (such as gas bubbles) to escape from the vicinity of detection electrodes 23/25.

Additionally, or in the alternative, gradient conditions may be generated by illuminating the sample on the detection array 7 with light from a light emission device 41 (FIG. 3, for example). By exciting the sample variants with light, the inherent energy of the sample biomolecules is altered, which in turn alters the reaction kinetic of the molecule. The gradient condition may be a gradient of wavelengths of light, such as can be produced by prismatic or other diffractional filtering of broadband light, or a gradient of intensities of light, such as can be produced by illuminating the substrate obliquely or by interposing an optical filter with a gradient of absorptive density.

In a preferred embodiment, the support 33 can be comprised of or include a tunable laser diode which emits light of a selected wavelength and intensity, for example. The light is directed onto the substrate upper surface area 11 so as to modulate the kinetics of binding between the sample variants and the reactant. Alternatively, the light may be generated by a tunable gas laser such as a nitrogen laser, located separately from the support 33 or substrate 9. A separate light source 41 would preferably be oriented so as to evenly illuminate the reaction chamber 37. In either case, the wavelength of the light would preferably be selected to be a wavelength that is absorbed by the reactant or variants to be assayed so that the absorption of photons would change the energy state of the molecule and, hence, the kinetics of the reaction being assayed.

All electrodes and light source 41 are connected to control electronics 43. The control electronics preferably include conventional electronic circuitry for the creation of the desired pH gradient by gradient electrodes, the measurement of the pH gradient so produced via detection electrodes (as potentiostatic measurements) relative to the reference electrode. The control electronics preferably also include conventional electronics to direct and control the light source (wavelength and intensity) and also to measure the rate of reactions between the reactant and variants by potentiostatic or any other electrochemical means of detection suitable for the nature of the chemical reaction occurring.

Photochemical Detection

In an alternate embodiment of the invention, detection of the reaction products and/or reaction kinetics is accomplished by photochemical means (FIG. 3).

In this embodiment, the gradient conditions may be created by at least one pair of gradient electrodes 17/19 spaced a distance apart on a gradient axis 21 along the substrate upper surface area 11. As above, a reaction chamber 37 is created between the substrate upper surface area 11 and a sample distributor 35, such that a sample is spread over reactants. In this embodiment, one or more reactants 3 are deposited in discrete regions on the substrate upper surface area 11. This arrangement permits multiple reactants to be subjected simultaneously to similar gradient conditions. In the example shown, the reactant 3 is arranged in discrete reactant areas running substantially parallel to a gradient axis 21 between the gradient electrodes 17/19.

Additionally, or in the alternative, gradient conditions may be generated by providing a light emission device 41 to illuminate the substrate from above as illustrated.

In use, the sample is applied to the reaction chamber 37 and contacts the reactant regions under a pH gradient applied via the gradient electrodes and under light conditions applied via the light source 47. As a chemical reaction proceeds at varying rates in varying positions along the reactant regions, the local concentration or binding of reactants or reaction products causes changes in the color and/or luminance of light emitted or absorbed by the reactants or indicator molecules bound to the reactants or otherwise participating in or affected by the reaction. Many mechanisms are commonly employed in the art to produce or enhance such photochemical changes in response to changes in binding, conformation, electrical charge or pH associated with chemical reactions, including molecules whose wavelength of fluorescence changes, molecules whose wavelengths of light absorption change, and molecules that change the degree or manner in which they polarize or change the rotation of polarized transmitted light, as described above.

In this embodiment, the detection of regional photochemical changes occurring in the proximity of the reaction chamber 37 can be detected by an imaging device 45 preferably spaced a distance from the substrate 9. The imaging device 45 may be, a video camera with a suitable sensitivity which records time-varying signals by control electronics, for example. The light source 41 may be used to provide illumination for the imaging process or it may be advantageous to use a separate illumination source 47, whose light may be modified by one or more filters 49 to change the bandwidth, polarization, or intensity of the illuminating light, either statically or dynamically according to signals from control electronics. In this embodiment, the substrate 9 may be made of glass, quartz or another transparent material to permit use of transmitted light from an illumination source 47, as illustrated in FIG. 3.

Local groups of pixels in the sequential images from imaging device 45 and recorded by control electronics 43 are processed by digital image analysis 51 to determine their correspondence to the various reactant regions and to the local pH levels along those regions. It is advantageous to employ fiduciary marks and specialized, known materials in one or more reactant regions to act as calibration signals for spatial dimensions, light intensity and the applied pH gradient. For example, one of the strips of reactant 3 shown in FIG. 3 could be composed of a dye whose color changes according to pH.

Thermal Gradients

Alternatively, or in addition to the use of electrical or light gradients, temperature gradients may be used to create a range of different conditions for the reaction to be measured on the detection array.

By way of example, a resistive heater could be attached to one edge of substrate 9 or incorporated upon the substrate surface area 11 or within the substrate thickness 15 to provide regional warming of the substrate 9, such that the sample in the reaction chamber 37 would likewise be regionally heated. Additionally, or in the alternative, an infrared source 41b may be directed at the reaction chamber thereby regionally heating or cooling the sample, thereby altering the reaction by direct photon absorption by the biomolecules. The kinetics of most biochemical reactions are affected strongly by the ambient temperature, a phenomenon usually described quantitatively as Q10, the change in rate of reaction for a 10 degree Celsius change in temperature.

In these embodiments, the rate of reaction between variants and reactants could be assayed by imaging a dye change that produces either a change in spectral absorption or fluorescent emission detected by an imaging device 45, for example. The rate of reaction could be measured in a substrate on which was imposed a two dimensional gradient, with a pH gradient at a second axis, preferably perpendicular to the first axis.

Data Analysis

In the operation of some embodiments, control electronics 43 produce a set of time-varying signals that control the ambient temperature, pH, and/or light intensity and wavelength illuminating said reactions, according to a sequence that has been determined empirically to produce a range of conditions that affects differentially the binding or reaction between the various variant biomolecules to be distinguished and the reactant. In addition to the effects of temperature, pH and the light, the kinetics of the reaction product production depends on the concentrations of the variants and reaction products, which change as a result of irreversible binding, hydrolysis, enzymatic degradation, photolysis or other consumptive reactions.

In all of the above described embodiments, the sensing method used to measure the amount or rate of binding or reaction produces a three dimensional matrix of data that is recorded by control electronics 43. Two dimensions of that matrix represent the physical place on a planar substrate at which a measurement was made and the third dimension represents the time at which a measurement was made. The physical place is correlated with the local value of the gradient(s) of conditions applied across the substrate. The time-varying signal at each location represents the amount or rate of reaction under the conditions prevailing at that place, which conditions themselves may be systematically varied in time according to the preprogrammed operation of control electronics 43.

By way of example, simple calculation demonstrates the use of multiple measurements from a gradient of imposed conditions to identify the absolute concentration of each of two variants ($V_1$ and $V_2$) of a biochemical that produces product (P) as a result of interacting with reactant (R), which is present in an excess quantity. The rate of reaction of each variant ($k_{n1}$) is assumed to vary as a function of the pH at the reaction site, according to the relationships:

$$V_1 + R \xrightarrow{k_1} P; k_1 = 1 + 0.1 \text{ pH}$$

$$V_2 + R \xrightarrow{k_2} P; k_2 = 1 + 0.2 \text{ pH}$$

Suppose that two measurement sites A and B are available, each of which produces a measurement of the rate of generation of product $P_A$ and $P_B$, respectively. Suppose that the pH at site A=7 and the pH at site B=8. Then the following measurements will be obtained:

$$P_A = 1.7[V_1] + 2.4[V_2]$$

$$P_B = 1.8[V_1] + 2.6[V_2]$$

Each equation can be solved for either $V_1$ or $V_2$:

$$[V_1] = (P_A - 2.4[V_2])/1.7 = (P_B - 2.6[V_2])/1.8$$

$$[V_2] = (P_A - 1.7[V_1])/2.4 = (P_B - 1.8[V_1])/2.6$$

By mutual substitution and simplification, these equations can be solved for:

$$[V_2] = 10(1.8 P_A - 1.7 P_B)$$

$$[V_1] = 10(2.6 P_A - 2.4 P_B)$$

In the example above, the values of $k_1$ and $k_2$ and their dependencies on pH were known a priori. In actual use, these values may not be known or they may be influenced by factors other than pH, e.g. temperature. In such situations, known admixtures of $V_1$ and $V_2$ could be used to calibrate the measurement system empirically for a wider range of gradient conditions, e.g., imposing a gradient of temperature orthogonal to the pH gradient and recording the output of sensors at many different combinations of ambient conditions in those two gradients. It is also likely that other biochemicals present in the sample may cross-react weakly with the reactant, producing a set of noisy results that cannot be reconciled absolutely with calibrations obtained using admixtures of the pure variants. In that case, pattern recognition techniques such as neural networks can be applied to compare the pattern of sensor signals obtained with the unknown sample to patterns of signals obtained with the calibration samples. Such pattern recognition techniques, once calibrated or trained, tend to compute a result that best fits all of the available data.

This results in a rich set of data whose patterns are interpreted by an analysis system 51. The analysis system 51 may perform this task by a variety of methods, including, but not limited to, a trained human observer examining a visual display of the reaction-rate dependencies, a computer program running "expert system" software that emulates the analytical processes of a trained human observer, a computer program running "neural network" software that has been trained to recognize the various patterns in the data by exposing it to patterns produced by samples containing known quantities of the various variants to be assayed.

It will be apparent to one skilled in the art that the nature of the reactant, the electrical or photo detection means employed and the design of control electronics and analysis system will depend on the nature of the specific variants to be detected. Furthermore, it is known that the conditions under which the reactions are performed should be tailored to those that produce the widest range of distinguishing signals for analysis system. This includes, for example, selecting the quantity of variants, the volume of the sample, the amount and starting pH of buffer in the sample, the range and steepness of the pH gradient produced by the gradient electrodes, the range of wavelengths of light applied, the dispersions of those wavelengths, the intensity of the light, the temperature under which the reactions occur, and other variables that are commonly manipulated in analytical chemistry. Simplified versions of this invention may be sufficient in some circumstances, for example, where the effects of temperature, pH or light absorption but not all are used to modulate the reactions sensed and analyzed by the invention.

The present invention can also be combined with other currently available biomolecule detection methods. Such methods may be used to isolate sample variants for use in this invention. For example, gel electrophoresis is a commonly used method for nucleic acid and protein identification and isolation. However, a specific band in a gel may contain more than one variant of the nucleic acid or protein of interest, that is, the variations are slight enough to affect the biomolecule's function yet not enough to be resolved by gel electrophoresis. Following gel-isolation, specific variants in the sample containing the mixture of biomolecules can then be identified using the methods and apparatuses described herein.

EXAMPLES

The present invention, by its ability to detect slight variations in biomolecules, will be advantageous in the diagnosis of diseases where ability to discern or quantify specific molecules is desired.

The present invention can be used to discriminate or quantify differences within a family of naturally occurring proteins in a patient. For example, classes of immunological, endocrine, growth factor, as well as signaling molecules which are difficult to discriminate using present techniques based primarily on, for example, molecular weight or isoelectric focusing, will be discernible at the amino-acid difference level without the need for laborious or time-consuming sequencing methodologies. In many cases, as previously stated, the "mutant" or non-native form(s) of a protein closely resembles the "normal" or native version of the protein, which are difficult to distinguish using prior methodologies. Examples molecules having clinical significance include hemoglobin (in which mutations cause various forms of anemia), dopamine receptors (in which mutations cause behavioral changes), Huntingtin (the protein in which mutations result in Huntington's disease) and dystrophin (the protein in which mutations result in muscular dystrophy).

These detection methods can also aid in the evaluation of various medical treatments, such as hormone replacement therapies as well as the efficacy of gene therapy. More specifically, the methods and elements in the present invention can be utilized to monitor the presence, expression levels and/or function of therapeutic proteins in an organism that has undergone treatment such as, for example, gene therapy. For example, a patient who suffers from a lack of a specific gene, or a deficit of sufficient levels of a requisite protein can be monitored post-gene therapy treatment using the methods described herein to verify that the gene therapy is successful.

As another example, the present invention can be used to detect proteins having abnormal conformations, for example, prion proteins. Prions are proteins that contain sequences that are similar, if not identical, to normal versions of a protein of interest, but by some unknown mechanism, are folded into atypical, detrimental structures. Prions are associated with diseases such as Creutzfeldt-Jakob Disease as well as Bovine Spongiform Encephalopathy or "mad cow disease." The misfolded proteins (prions) associated with these pathologies can be detected in various organisms by utilizing the present invention to detect the presence of these abnormal protein populations, long before any outwardly obvious symptoms are manifested (usually several years). However, it is within the scope of the present invention, that the electrochemical or photochemical methods described herein can be utilized for detecting any biomolecule based on its reactivity or chemical reaction with, for example, a substrate.

It is also within the scope of the present invention, that non-protein molecules can be detected based on their reactivity with a substrate. For example, the HIV as well as Hepatitis viruses are known to exist in different infectious forms. The ability to distinguish between whether an individual is infected with, for example, the Hepatitis A, B, or C virus based on its selective reactivity with a substrate can aid in identifying the prognosis and/or the preferred mode of treatment most efficacious for the particular viral strain.

It is considered within the scope of the present invention that the apparatus and teachings disclosed herein may be utilized whenever the discrimination of similar biomolecules in an admixture is required.

This application contains references to patents which are appended and each of which is hereby incorporated by reference in its entirety.

What is claimed is:

1. A method for the identification and quantification of admixtures of at least a first and a second biomolecular variant comprising: applying at least one condition gradient upon a detection array along a gradient axis having discrete locations, wherein the gradient conditions affect at least one of the rate of binding or reaction between the variants and at least one reactant; measuring the rate of binding or reaction between the variants and the at least one reactant at the discrete locations along the gradient axis at discrete times; and analyzing measurements of the rate of binding or reaction from the discrete locations along the gradient axis at discrete times to determine the quantities of each of the first and a second biomolecular variant present in the admixture.

2. The method of claim 1, further comprising applying a second condition gradient upon the detection array along a second gradient axis, wherein the gradient conditions affect the rate of binding or reaction between the variants and the at least one reactant.

3. The method of claim 2 wherein the second gradient axis is perpendicular to the first condition gradient.

4. The method of claim 1, wherein the at least one condition gradient is selected from the group comprising a pH gradient, a light absorption gradient or a temperature gradient.

5. A method for the discrimination of biomolecules in an admixture comprising the steps of:
   a. obtaining a sample comprising at least a first and a second biomolecule;
   b. exposing the sample to at least one gradient condition along a gradient axis to alter the inherent charge of the biomolecules;
   c. contacting the biomolecules with at least one reactant to cause the formation of at least one reaction product; and d. detecting at least one of a rate of binding between the biomolecules and the at least one reactant or a rate of reaction between the variants and the at least one reactant at discrete locations along the gradient axis.

6. A method for the discrimination of biomolecules in an admixture comprising the steps of:
   a. obtaining a sample comprising at least first and a second biomolecule;
   b. exposing the sample to at least one gradient condition along a gradient axis to alter the inherent energy of the biomolecules;
   c. contacting the biomolecules with at least one reactant to cause the formation of at least one reaction product; and
   d. detecting at least one of a rate of binding between the biomolecules and the at least one reactant or a rate of reaction between the variants and the at least one reactant at discrete locations along the gradient axis.

7. A method for the discrimination of biomolecules in an admixture comprising the steps of:
   a. obtaining a sample comprising at least first and a second biomolecule;
   b. exposing the sample to at least one gradient condition along a gradient axis to alter the inherent energy and inherent charge of the biomolecules;
   c. contacting the biomolecules with at least one reactant to cause the formation of at least one reaction product; and
   d. detecting at least one of a rate of binding between the biomolecules and the at least one reactant or a rate of reaction between the variants and the at least one reactant at discrete locations along the gradient axis.

8. The method of claim 5, 6 or 7 further comprising the step of quantifying the amount of the first or the second biomolecule in the sample from the rate of binding between the biomolecules and the at least one reactant or a rate of reaction between the variants and the at least one reactant measured at discrete locations along the gradient axis at discrete time periods.

9. The method of claim 5 or 7 wherein the gradient condition used to alter the inherent charge of the biomolecules is a pH gradient.

10. The method of claim 6 or 7 wherein the gradient condition used to alter the inherent energy of the biomolecules is light absorption.

11. The method of claim 1 wherein the reaction product is detected using electrochemical detectors.

12. The method of claim 1 wherein the reaction product is detected using photochemical detectors.

13. The method of claim 1 wherein the biomolecules are selected from the group comprising proteins, deoxyribonucleic acids, ribonucleic acids or prions.

* * * * *